(12) United States Patent
Yukimoto (10) Patent No.: US 9,415,129 B2
(45) Date of Patent: Aug. 16, 2016

(54) MOVING HANDRAIL DISINFECTING DEVICE FOR PASSENGER CONVEYOR

(71) Applicant: Toshihiro Yukimoto, Osaka (JP)

(72) Inventor: Toshihiro Yukimoto, Osaka (JP)

(*) Notice: Subject to any disclaimer, the term of this patent is extended or adjusted under 35 U.S.C. 154(b) by 472 days.

(21) Appl. No.: 14/138,938

(22) Filed: Dec. 23, 2013

(65) Prior Publication Data

US 2014/0186219 A1  Jul. 3, 2014

(30) Foreign Application Priority Data

Dec. 28, 2012 (JP) ................................ 2012-288872
Aug. 23, 2013 (JP) ................................ 2013-172801

(51) Int. Cl.

| A61L 2/24 | (2006.01) |
|---|---|
| A61L 2/26 | (2006.01) |
| A61L 2/18 | (2006.01) |
| B66B 31/02 | (2006.01) |

(52) U.S. Cl.
CPC ... *A61L 2/26* (2013.01); *A61L 2/18* (2013.01); *A61L 2/24* (2013.01); *B66B 31/02* (2013.01)

(58) Field of Classification Search
CPC ............... A61L 2/18; A61L 2/24; A61L 2/26; B66B 31/02
USPC ......................................................... 198/495
See application file for complete search history.

(56) References Cited

FOREIGN PATENT DOCUMENTS

| JP | 5-51194 | 3/1993 |
|---|---|---|
| JP | 5-338984 | 12/1993 |
| JP | 8-119569 | 5/1996 |
| JP | 2002-205890 | 7/2002 |
| JP | 2004-113729 | 4/2004 |
| JP | 2004-277462 | 10/2004 |
| JP | 2005-132532 | 5/2005 |
| JP | 2007-314298 | 12/2007 |
| JP | 2008-63103 | 3/2008 |
| JP | 2008-280141 | 11/2008 |
| JP | 2011-121664 | 6/2011 |
| JP | 2012-197154 | 10/2012 |

*Primary Examiner* — Timothy Cleveland
(74) *Attorney, Agent, or Firm* — Wenderoth, Lind & Ponack, L.L.P.

(57) ABSTRACT

A moving handrail disinfecting device for passenger conveyor whereby disinfection solutions can be suitably used depending on the situations of the device and the like, resulting in appropriate disinfection treatment with little waste, is a moving handrail disinfecting device 10B, having a contact roller switching unit comprising an applying roller 17 to be allowed to make contact with the surface of a moving handrail 5, a first impregnating roller 18 and a second impregnating roller 19 which supply disinfection solutions, a first slide section 22A, a second slide section 22B and a sliding mechanism 23A which separately slides the both, wherein a control unit 60B controls the sliding mechanism 23A to separately slide the first slide section 22A and the second slide section 22B so as to switch a roller to be allowed to make contact with the applying roller 17 from the first impregnating roller 18 to the second impregnating roller 19, or from the second impregnating roller 19 to the first impregnating roller 18, when a prescribed switching condition was satisfied.

12 Claims, 4 Drawing Sheets

MOVING HANDRAIL DISINFECTING DEVICE FOR PASSENGER CONVEYOR

BACKGROUND OF THE INVENTION

1. Field of the Invention

The present invention relates to a moving handrail disinfecting device for passenger conveyor, and more particularly, to a moving handrail disinfecting device for passenger conveyor which can disinfect moving handrails of passenger conveyors such as escalators and moving pavements.

2. Description of the Relevant Art

In the public facilities and commercial facilities such as the stations and department stores, escalators are placed. An escalator has endless moving handrails which circuit in synchronism with steps (treadboards) on which users stand on both sides thereof. In order to use the escalator safely, the users preferably get on the steps with holding onto the moving handrail and keep on holding onto the moving handrail until they get off.

However, since the moving handrails of the escalators are held by large numbers of the general public, some of the users do not like to touch the moving handrails. Especially in the season of the spread of influenza or the like, there are a lot of users who get on the escalators with trying not to touch the moving handrails thereof in fear of a virus infection through the medium of the moving handrails.

Therefore, disinfecting devices for moving handrails of passenger conveyors have been proposed. For example, in the below-mentioned Patent Document 1, a device has been disclosed, having a roller which disinfects the surface of a moving handrail in the vicinity of an inlet of the moving handrail within a truss. Using this disinfecting device, when a user who came to a landing of an escalator is detected by a sensor, the moving handrail is disinfected by allowing the roller to make contact with the moving handrail only during the interval that the moving handrail makes a circuit.

However, using the disinfecting device described in the Patent Document 1, every time a user of the escalator is detected, the disinfection by the roller is conducted. As a result, in places where there are a lot of passengers, the disinfection by the roller is likely to be continuously conducted. Therefore, there is a problem that the roller and associated parts which make contact with the moving handrail are quickly deteriorated. Moreover, since the roller is arranged within the truss, there is another problem that maintenance work such as replacement of those parts is not easy to perform.

Using the disinfecting device described in the Patent Document 1, since the disinfection is conducted without regard to a sticking state of dirt (tiny dirt such as dust, oil element, etc.), viruses and the like to the moving handrail, the frequency of refilling of a disinfection solution and that of replacement of the roller tend to be high, leading to a problem of a high maintenance cost.

In the case of a large facility, a dozen or more escalators are placed in the whole facility. Supposing that the disinfecting devices described in the Patent Document 1 are installed on every escalator in such facility, since the number of users of each escalator varies depending on its arranged place, the disinfecting devices installed on each escalator vary in degree of deterioration of the roller and that of dirt, and in decrease of the disinfection solution and the like. However, since these situations of each disinfecting device cannot be seen from the outside of the disinfecting device, it is necessary to uniformly perform maintenance work on every disinfecting device.

Therefore, since the burden of such maintenance work is heavy and it is impossible to appropriately manage every disinfecting device, it is difficult to actually install such disinfecting devices.

Patent Document 1: Japanese Patent Application Laid-Open Publication No. 2011-121664

SUMMARY OF THE INVENTION

The present invention was developed in order to solve the above problems, and it is an object of the present invention to provide a moving handrail disinfecting device for passenger conveyor, whereby appropriate disinfection treatment with little waste depending on situations can be conducted, and information concerning the device can be centrally managed in a management center so as to enhance shareability of information and maintenance performance.

In order to achieve the above object, a moving handrail disinfecting device for passenger conveyor according to a first aspect of the present invention is characterized by being a moving handrail disinfecting device, comprising a disinfecting unit for disinfecting a moving handrail of a passenger conveyor, being installed outside at least one of handrail inlets on each side of drawing and delivery of said moving handrail, and a control unit operable to control disinfection operations by the disinfecting unit based on prescribed operating conditions, the disinfecting unit comprising an applying roller to be allowed to make contact with the moving handrail, a first impregnating roller to be allowed to make contact with said applying roller to supply a first disinfection solution, a second impregnating roller to be allowed to make contact with the applying roller to supply a second disinfection solution, and a contact roller switching unit operable to switch a roller to be allowed to make contact with the applying roller to the first impregnating roller or the second impregnating roller, said contact roller switching unit comprising a first slide section on which a first disinfection solution tab with the first impregnating roller arranged is placed, a second slide section on which a second disinfection solution tab with the second impregnating roller arranged is placed, and a sliding mechanism operable to separately slide the first slide section and the second slide section, wherein the control unit has a function of controlling the sliding mechanism to slide the first slide section and the second slide section so as to switch the roller to be allowed to make contact with the applying roller to the first impregnating roller or the second impregnating roller, when a prescribed switching condition was satisfied.

By the moving handrail disinfecting device for passenger conveyor according to the first aspect of the present invention, when the prescribed switching condition was satisfied, by controlling the sliding mechanism to separately slide the first slide section and the second slide section, the roller to be allowed to make contact with the applying roller can be switched from the first impregnating roller to the second impregnating roller, or from the second impregnating roller to the first impregnating roller. As a result, it becomes possible to suitably use two kinds of disinfection solutions depending on the situations of the disinfecting device concerned and the like, leading to appropriate disinfection treatment with little waste depending on the situations.

For example, under normal conditions, by allowing the first impregnating roller to make contact with the applying roller so as to impregnate the applying roller with the first disinfection solution through the first impregnating roller, the disinfection of the moving handrail with the first disinfection solution is conducted. When the switching condition was satisfied, by switching the roller to be allowed to make contact with the applying roller from the first impregnating roller to the second impregnating roller so as to impregnate the applying roller with the second disinfection solution through the second impregnating roller, the disinfection of the moving handrail with the second disinfection solution can be conducted. By such sliding construction, the device can be made compact even with the first impregnating roller and the second impregnating roller.

The moving handrail disinfecting device for passenger conveyor according to a second aspect of the present invention is characterized by further comprising an elevating unit operable to raise and lower the disinfecting unit in a manner that can selectively allow the applying roller to make contact with the moving handrail, wherein the control unit has a function of controlling the sliding mechanism to slide the first slide section and the second slide section and then controlling the elevating unit to raise the disinfecting unit until the applying roller is pressed against the moving handrail in the moving handrail disinfecting device for passenger conveyor according to the first aspect of the present invention.

By the moving handrail disinfecting device for passenger conveyor according to the second aspect of the present invention, by controlling the sliding mechanism, the first slide section and the second slide section are slid, and thereafter, by controlling the elevating unit, the disinfecting unit can be raised until the applying roller is pressed against the moving handrail. As a result, it becomes possible to suitably use two kinds of disinfection solutions depending on the situations of the disinfecting device concerned and the like, as well as intermittently conduct the applying roller's contact with (disinfection of) the moving handrail, leading to appropriate disinfection treatment with less waste depending on the situations.

The moving handrail disinfecting device for passenger conveyor according to a third aspect of the present invention is characterized by bearing portions of the applying roller, bearing portions of the first impregnating roller and bearing portions of the second impregnating roller, being constructed in a manner that give rotation sliding resistance to the rotation movement of each of the rollers in the moving handrail disinfecting device for passenger conveyor according to the first or second aspect of the present invention.

By the moving handrail disinfecting device for passenger conveyor according to the third aspect of the present invention, since the bearing portions of the applying roller, the bearing portions of the first impregnating roller and the bearing portions of the second impregnating roller are constructed in a manner that give the rotation sliding resistance to the rotation movement of each of the rollers, the rotation rate of the applying roller can be regulated to be slower than the moving rate of the moving handrail. As a result, it is possible to cause the rotation sliding resistance (a slippage state) between the applying roller and the moving handrail, leading to improvements in efficiency of applying disinfection solutions, that of removing dirt and the like.

The moving handrail disinfecting device for passenger conveyor according to a fourth aspect of the present invention is characterized by further comprising a communications unit operable to send information obtained by said disinfecting device to an outside management center, and a dirt detecting unit operable to detect dirt on the surface of the moving handrail, wherein the control unit controls the timing and time of a disinfection operation by the disinfecting unit based on the state of dirt detected by the dirt detecting unit, as well as controls the communications unit to send information about the state of dirt detected by the dirt detecting unit to the management center in the moving handrail disinfecting device for passenger conveyor according to any one of the first to third aspects of the present invention.

When the moving handrail disinfecting device for passenger conveyor according to the fourth aspect of the present invention is used, since various kinds of information obtained by the disinfecting device concerned can be sent to the outside management center by the communications unit, in the management center, for example, it becomes possible to centrally manage information about a plurality of disinfecting devices installed on each passenger conveyor in a facility. Therefore, it becomes possible to perform appropriate maintenance on every disinfecting device based on these information items, leading to enhanced shareability of information and maintenance performance.

Since the timing and time of a disinfection operation by the disinfecting unit is controlled based on the state of dirt detected by the dirt detecting unit, it is possible to conduct disinfection of the moving handrail at an appropriate frequency based on the state of dirt. As a result, it is possible to prevent disinfection treatment from being conducted more than necessary, leading to a reduction in maintenance cost such as disinfection solution cost. In the management center, information about the state of dirt detected by the dirt detecting unit of each disinfecting device can be managed, and therefore, it becomes possible to perform required maintenance with proper timing on every disinfecting device.

The moving handrail disinfecting device for passenger conveyor according to a fifth aspect of the present invention is characterized by further comprising a communications unit operable to send information obtained by said disinfecting device to an outside management center, and a passenger number detecting unit operable to detect the number of persons boarding the passenger conveyor, wherein the control unit controls the timing and time of a disinfection operation by the disinfecting unit based on the accumulated number of passengers detected by the passenger number detecting unit, as well as controls the communications unit to send information about the accumulated number of passengers detected by the passenger number detecting unit to the management center in the moving handrail disinfecting device for passenger conveyor according to any one of the first to third aspects of the present invention.

By the moving handrail disinfecting device for passenger conveyor according to the fifth aspect of the present invention, since the timing and time of a disinfection operation by the disinfecting unit is controlled based on the accumulated number of passengers detected by the passenger number detecting unit, it is possible to conduct disinfection of the moving handrail at an appropriate frequency based on the accumulated number of passengers. As a result, it is possible to prevent disinfection treatment from being conducted more than necessary, leading to a reduction in maintenance cost such as disinfection solution cost. In the management center, the accumulated number of passengers detected by the passenger number detecting unit of each disinfecting device can be managed, and therefore, it becomes possible to perform required maintenance with proper timing on every disinfecting device.

The moving handrail disinfecting device for passenger conveyor, according to a sixth aspect of the present invention is characterized by further comprising a communications unit operable to send information obtained by said disinfecting device to an outside management center, and a handrail contact detecting unit operable to detect a contact of a part of a body with the moving handrail, wherein the control unit controls the timing and time of a disinfection operation by the disinfecting unit based on the detection state of handrail contact detected by the handrail contact detecting unit, as well as controls the communications unit to send information about the detection state of handrail contact detected by the handrail contact detecting unit to the management center in the moving handrail disinfecting device for passenger conveyor according to any one of the first to third aspects of the present invention.

By the moving handrail disinfecting device for passenger conveyor according to the sixth aspect of the present invention, since the timing and time of a disinfection operation by the disinfecting unit is controlled based on the detection state of handrail contact detected by the handrail contact detecting unit, it is possible to separately conduct disinfection of each moving handrail arranged on the right and left sides at an appropriate frequency based on the detection state of handrail contact, such as the accumulated number of persons who made contact with the moving handrail. As a result, it is possible to prevent disinfection treatment from being conducted more than necessary, leading to a reduction in maintenance cost such as disinfection solution cost. In the management center, the detection state of handrail contact detected by the handrail contact detecting unit of each disinfecting device can be managed, and therefore, it becomes possible to perform required maintenance with proper timing on every disinfecting device.

The moving handrail disinfecting device for passenger conveyor according to a seventh aspect of the present invention is characterized by further comprising a communications unit operable to send information obtained by said disinfecting device to an outside management center, and a virus detecting unit operable to detect a prescribed virus sticking to the surface of the moving handrail, wherein the control unit controls the timing and time of a disinfection operation by the disinfecting unit based on the detection state of the virus detected by the virus detecting unit, as well as controls the communications unit to send information about the detection state of the prescribed virus detected by the virus detecting unit to the management center in the moving handrail disinfecting device for passenger conveyor according to any one of the first to third aspects of the present invention.

Using the moving handrail disinfecting device for passenger conveyor according to the seventh aspect of the present invention, since the timing and time of a disinfection operation by the disinfecting unit is controlled based on the detection state of the virus detected by the virus detecting unit, it is possible to conduct sufficient disinfection with good timing in the case of high necessity of disinfection on public health, according to the detection state of the virus, for example, in a case where the influenza virus, the noro-virus or the like was detected, leading to an improvement in public health. In the management center, the detection state of the virus detected by the virus detecting unit of each disinfecting device can be managed, and therefore, it becomes possible to know which passenger conveyor highly needs to be disinfected and to perform required maintenance such as replacement with a suitable disinfection solution with proper timing on every disinfecting device.

DESCRIPTION OF THE PREFERRED EMBODIMENTS

Figure 1:
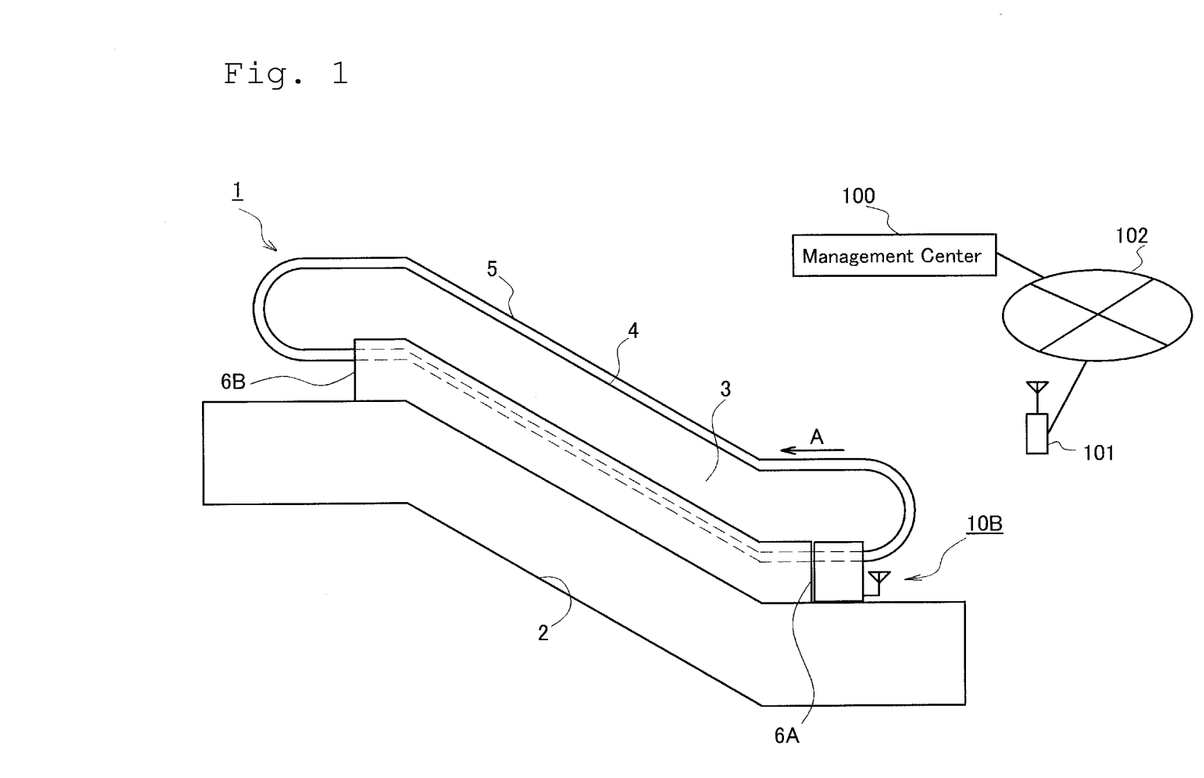
FIG. 1 is a side view schematically showing the main part of a passenger conveyor equipped with a moving handrail disinfecting device for passenger conveyor according to an embodiment of the present invention.

The preferred embodiments of the moving handrail disinfecting device for passenger conveyor according to the present invention are described below by reference to the Figures noted above. FIG. 1 is a side view schematically showing the main part of an escalator equipped with a moving handrail disinfecting device for passenger conveyor (hereinafter, referred to as a moving handrail disinfecting device) according to an embodiment.

An escalator 1 comprises a foundation (hereinafter, referred to as a truss) 2 built with a steel frame which supports the whole escalator from the bottom, wherein a lot of steps (not shown) moving in a line between the upper floor and the lower floor are arranged. These not shown steps are members having treadboard surfaces which users get on. Within the truss 2, a driving unit (not shown) including a motor, a speed reducer and associated parts, and an escalator control unit (not shown) which controls the whole escalator including said driving unit are also arranged.

On both sides of the not shown steps arranged in the truss 2, balustrades 3 made of a metal plate or a resin plate each stand. On the outer peripheral portion of the balustrade 3, a guide rail 4 is arranged, and an endless moving handrail 5 is caused to circuit in synchronism with the not shown steps along this guide rail 4. Users can get on the escalator 1 by standing on the not shown steps with holding onto the moving handrail 5.

Here, a case wherein the escalator 1 is going up, that is, a case wherein the moving handrail 5 is moving in the direction of an arrow A is described.

The moving handrail 5 goes through an inlet part (delivery inlet) 6A on the lower floor side (handrail delivery side) of the truss 2 to the outside of the truss 2, turns up in a landing of the lower floor, moves along the guide rail 4 on the upper peripheral portion of the balustrade 3 in the direction of the arrow A, turns down again in a landing of the upper floor, enters the truss 2 through an inlet part (drawing inlet) 6B formed on the upper floor side (handrail drawing side) of the truss 2, and circuits through the truss 2 to the inlet part 6A in the lower floor landing.

Outside both of the inlet parts 6A on the lower floor side, moving handrail disinfecting devices 10B each are installed. Here, the moving handrail disinfecting devices 10B are preferably installed outside the inlet parts 6A on the lower floor side in the case of an up-escalator, while outside the inlet parts 6B on the upper floor side in the case of a down-escalator, but the form of installation thereof is not limited to this. The moving handrail disinfecting devices 10B may be installed outside the inlet parts 6A and 6B on both of the upper and lower floor sides.

How to set the moving handrail disinfecting device 10B is not particularly limited. Attachment to the floor, attachment to the side surface of the inlet part 6A, or making a clip such as a heavy-duty clip on the top of the device by which one-touch attachment to the balustrade 3 is made possible, may be adopted.

The moving handrail disinfecting device 10B can exchange data with a management center 100 through a base station 101 and a communication network 102 such as the Internet communication network and a telephone network. The outside management center 100, corresponding to an information management center inside the facility wherein the escalator 1 is placed, or an information management center managing the escalator 1 outside the facility, comprises a computer system including a server and the like.

Figure 2:
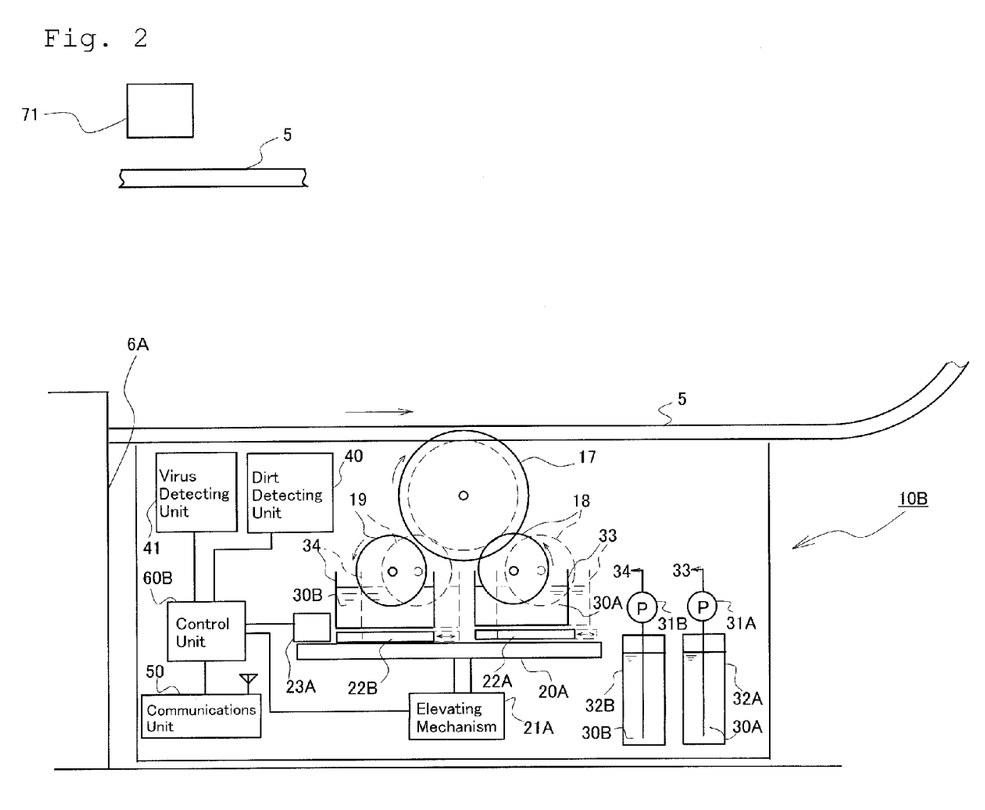
FIG. 2 is a side view schematically showing the main part of the moving handrail disinfecting device for passenger conveyor according to the embodiment.
Figure 3:
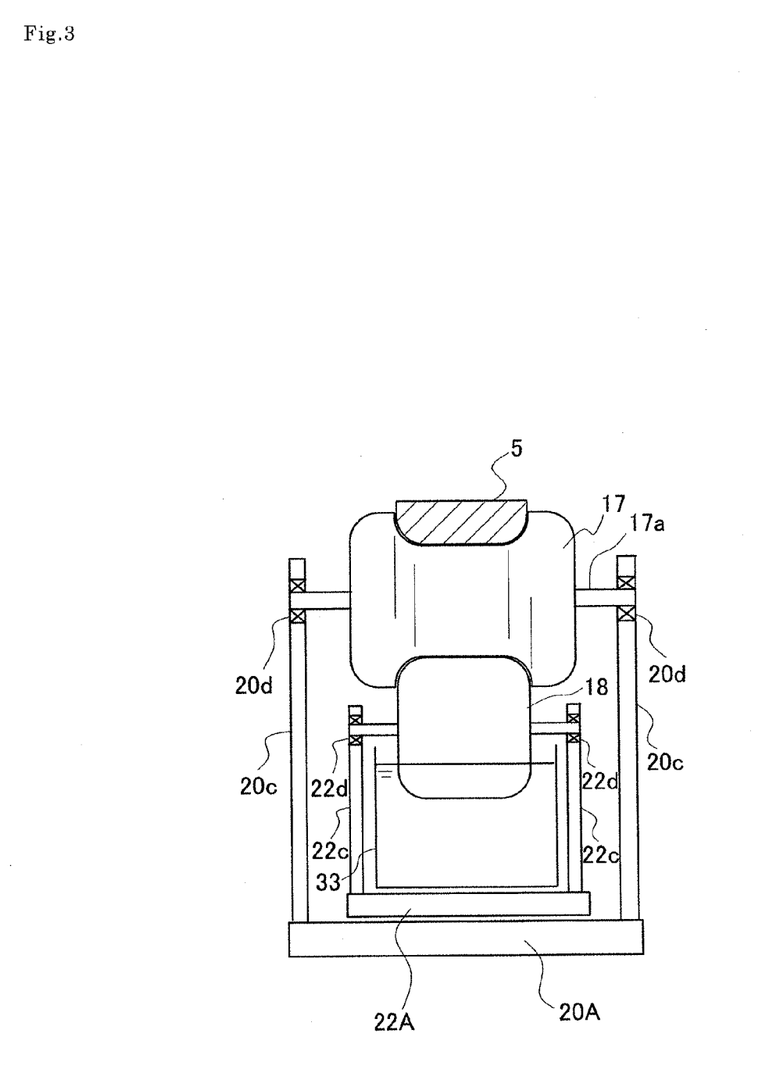
FIG. 3 is an elevation view schematically showing the main part in the vicinity of an applying roller of the moving handrail disinfecting device for passenger conveyor according to the embodiment.

FIG. 2 is a side view schematically showing the main part of the moving handrail disinfecting device 10B according to the embodiment. FIG. 3 is an elevation view schematically showing the main part in the vicinity of an applying roller of the moving handrail disinfecting device 10B according to the embodiment.

The moving handrail disinfecting device 10B comprises an applying roller 17, being allowed to make contact with the surface of the moving handrail 5 having an almost C-shaped section and rotate with the movement of the moving handrail 5, a first impregnating roller 18, being allowed to make contact with the surface of the applying roller 17 and rotate, so as to supply a first disinfection solution 30A to the applying roller 17, and a second impregnating roller 19, being allowed to make contact with the surface of the applying roller 17 and rotate, so as to supply a second disinfection solution 30B to the applying roller 17.

In this embodiment, the first impregnating roller 18 and the second impregnating roller 19 are arranged in a manner that rotate in the same direction as the applying roller 17, but it is also possible to arrange them in such a manner that they rotate in the opposite direction using a driving force such as a motor.

As shown in FIG. 3, the applying roller 17 is rotatably supported with a shaft through bearing portions 20d on side walls 20c which stand on a stand 20A moving up and down. The surface of the applying roller 17 is formed almost in a U-shape in a manner that makes contact with the surface of the moving handrail 5, and it can also be allowed to make contact with the side of the moving handrail 5 having an almost C-shaped section.

On the stand 20A, a first slide plate 22A is slidably arranged, and on the first slide plate 22A, a first disinfection solution tab 33 is arranged. On both sides of the first disinfection solution tab 33, side walls 22c stand on the first slide plate 22A.

The first impregnating roller 18 is rotatably supported with a shaft through bearing portions 22d on the side walls 22c, and a part thereof is impregnated in the first disinfection solution 30A in the first disinfection solution tab 33.

On the stand 20A, a second slide plate 22B is slidably arranged, and on the second slide plate 22B, a second disinfection solution tab 34 is arranged. On both sides of the second disinfection solution tab 34, side walls (not shown) stand on the second slide plate 22B.

The second impregnating roller 19 is rotatably supported with a shaft through bearing portions (not shown) on the side walls, and a part thereof is impregnated in the second disinfection solution 30B in the second disinfection solution tab 34.

The moving handrail disinfecting device 10B comprises an elevating mechanism 21A operable to raise and lower the stand 20A, and a sliding mechanism 23A operable to allow the first slide plate 22A and the second slide plate 22B to separately slide crossing at right angles to a rotating shaft 17a of the applying roller 17. As the construction of the elevating mechanism 21A or the sliding mechanism 23A, an electromagnetic actuator having a stretching mechanism, a motor-driven cam mechanism, or various kinds of driving mechanisms wherein a gear mechanism such as a worm gear or a rack and pinion and a motor are combined may be adopted.

A contact roller switching mechanism (a contact roller switching unit) which switches a roller to be allowed to make contact with the applying roller 17 to the first impregnating roller 18 or the second impregnating roller 19, comprises the first slide plate 22A, second slide plate 22B and sliding mechanism 23A. The disinfecting unit comprises the applying roller 17, first impregnating roller 18, and second impregnating roller 19, and said contact roller switching mechanism.

The bearing portions 20d of the applying roller 17, the bearing portions 22d of the first impregnating roller 18 and the bearing portions (not shown) of the second impregnating roller 19 are constructed in such a manner that rotation sliding resistance is given to the rotation movement of the rotation shaft of each roller. Because of this rotation sliding resistance, the rotation rate of the applying roller 17 is regulated to be slower than the moving rate of the moving handrail 5, and due to the effect of the rotation sliding resistance between the applying roller 17 and the moving handrail 5, the efficiency of applying the disinfection solution, that of removing dirt and the like are enhanced.

To the first disinfection solution tab 33, a first disinfection solution tank 32A is connected through a first pump 31A, and the first disinfection solution 30A is supplied to the first disinfection solution tab 33 from the first disinfection solution tank 32A with prescribed timing. For example, with the timing when it is detected that the liquid surface came to a predetermined level or lower by a not shown level sensor operable to detect the liquid surface level arranged within the first disinfection solution tab 33, the first disinfection solution 30A is supplied to the first disinfection solution tab 33.

To the second disinfection solution tab 34, a second disinfection solution tank 32B is connected through a second pump 31B, and the second disinfection solution 30B is supplied to the second disinfection solution tab 34 from the second disinfection solution tank 32B with prescribed timing. For example, with the timing when it is detected that the liquid surface came to a predetermined level or lower by a not shown level sensor operable to detect the liquid surface level arranged within the second disinfection solution tab 34, the second disinfection solution 30B is supplied to the second disinfection solution tab 34.

Different kinds of disinfection solutions are filled in the first disinfection solution tank 32A and the second disinfection solution tank 32B, respectively. As the first disinfection solution 30A, a disinfection solution (a cleaning solution) with a higher effect of removing dirt than the second disinfection solution 30B is used, while as the second disinfection solution 30B, a disinfection solution with better sterilization performance of viruses and the like than the first disinfection solution 30A is used.

As the second disinfection solution 30B, for example, an alcohol formulation having a high disinfecting/sterilizing property such as ethanol of a high concentration (about 70%-80%), a solution containing iodine of a prescribed concentration (e.g. about 0.05%-0.2%), a sodium hypochlorite solution of a prescribed concentration (e.g. about 0.01%-0.2%), a benzalkonium chloride solution of a prescribed concentration (e.g. about 0.05%0.1%) or the like is used.

The moving handrail disinfecting device 10B further comprises a dirt detecting unit 40 which detects the state of dirt sticking to the surface of the moving handrail 5. The dirt detecting unit 40 comprises an image sensor for visual inspections, an image processor and associated parts, having a function of continuously or periodically monitoring the state of foreign materials such as small dirt (dust) or oil element sticking to the surface and the degree (sticking range, sticking number, etc.) thereof, whereby detection signals of dirt and the like are output to a control unit 60B.

A virus detecting unit 41 has a function of detecting a prescribed virus (e.g. the influenza virus or the noro-virus) sticking to the moving handrail 5. Any method of detecting the virus using the virus detecting unit 41 may be adopted. For example, a detecting method such as immune-chromatography using an antigen detecting reagent of the influenza virus is adopted, wherein detection treatment (specimen sampling, specimen solution extraction, reaction treatment, decision treatment, etc.) is automatically performed. A virus detection signal detected by the virus detecting unit 41 is output to the control unit 60B.

A handrail sensor 71 is a sensor operable to detect a passenger's holding onto the moving handrail 5. The handrail sensors 71 each are arranged above the moving handrails 5 on both sides or on the side walls of the building in the vicinity of a landing of the escalator 1 or several steps forward from the landing. The handrail sensor 71 detects the existence of an object on the moving handrail 5 within a given detecting area, and using the handrail sensor 71, it is possible to detect passengers' holding onto the moving handrails 5 separately on both of the moving handrails 5. The handrail sensor 71 comprises an image sensor and an image processor, and a signal detected by the handrail sensor 71 is output to the control unit 60B.

The moving handrail disinfecting device 10B further comprises a communications unit 50 for communications with the outside management center 100. The communications unit 50 has a function of wireless communications which makes it possible to exchange data with the management center 100 through the base station 101 and the communication network 102 such as the Internet communication network and the telephone network shown in FIG. 1. Here, the communications unit 50 may also have a function of cable communications.

The control unit 60B conducts control of operations and control of sending/receiving of data on each of the elevating mechanism 21A, sliding mechanism 23A, first pump 31A, second pump 31B, dirt detecting unit 40, virus detecting unit 41, communications unit 50 and associated parts, comprising a not shown microcomputer, an input/output interface, a memory, a timer circuit, a power circuit and associated parts.

The control unit 60B has a control function of switching the roller to be allowed to make contact with the applying roller 17 from the first impregnating roller 18 to the second impregnating roller 19 when a virus was detected by the virus detecting unit 41 (a first switching condition), and a control function of switching the roller to be allowed to make contact with the applying roller 17 from the second impregnating roller 19 to the first impregnating roller 18 when the dirt state detected by the dirt detecting unit 40 came to a prescribed dirt state (a second switching condition).

Figure 4:
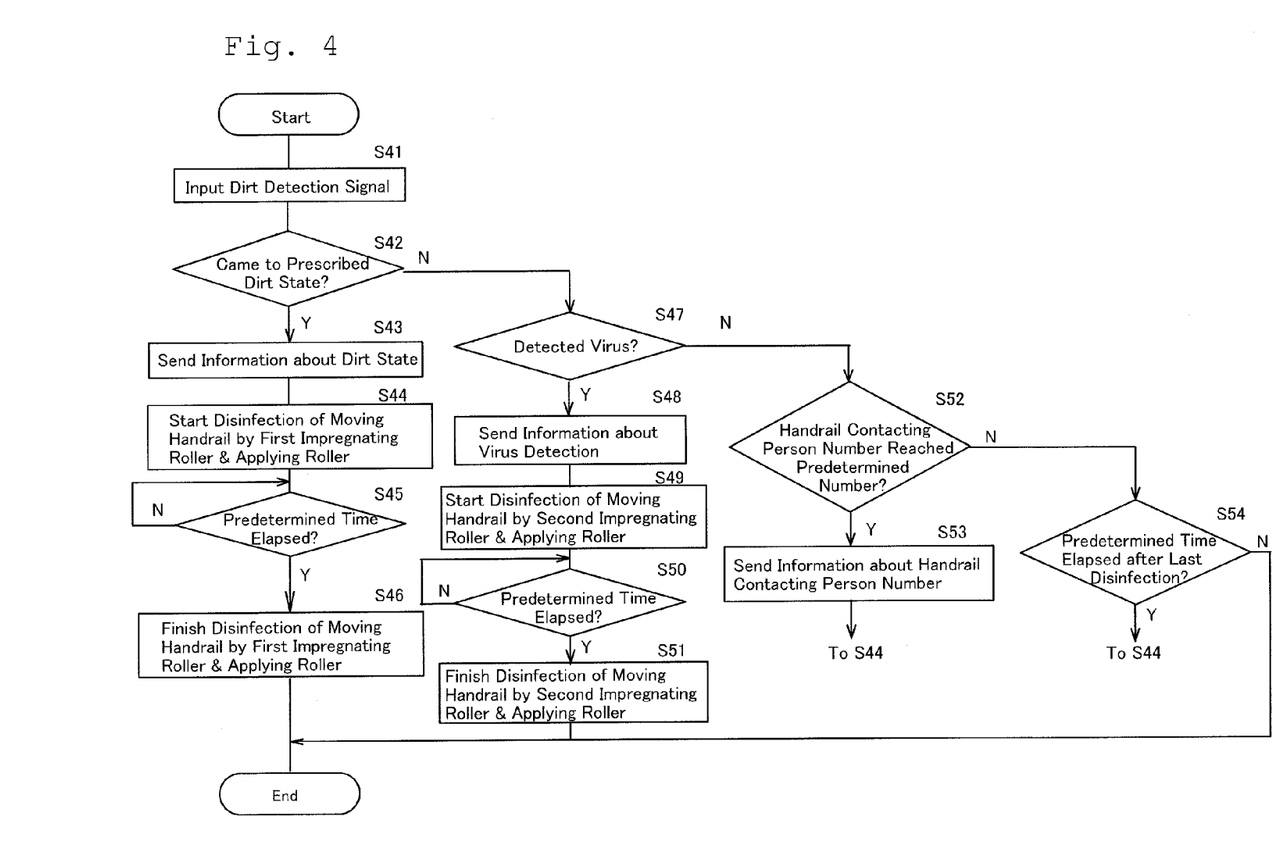
FIG. 4 is a flowchart showing a disinfection treatment operation conducted by a control unit in the moving handrail disinfecting device for passenger conveyor according to the embodiment.

FIG. 4 is a flowchart showing the disinfection treatment operation conducted by the control unit 60B in the moving handrail disinfecting device 10B according to the embodiment.

In Step S41, a dirt detection signal is input from the dirt detecting unit 41, and in Step S42, whether the surface of the moving handrail 5 came to the prescribed dirt state or not (e.g. whether the detected number of sticking foreign materials such as dirt reached a predetermined number after the last disinfection operation or not) is judged. When it is judged that it came to the prescribed dirt state (e.g. the detected number of sticking foreign materials reached the predetermined number), the operation goes to Step S43.

In Step S43, the communications unit 50 is controlled to send information concerning the dirt state (e.g. identification information about the device itself, elapsed time information after the last disinfection operation, and information including the detected number of sticking foreign materials) to the outside management center 100, and the operation goes to Step S44.

In Step S44, the disinfection (cleaning) treatment on the moving handrail 5 using the first impregnating roller 18 moistened with the first disinfection solution 30A and the applying roller 17 is started. That is, the sliding mechanism 23A is actuated to slide the first slide plate 22A in such a manner that the first impregnating roller 18 comes in contact with the applying roller 17, while to slide the second slide plate 22B in such a manner that the second impregnating roller 19 does not come in contact with the applying roller 17.

Thereafter, the elevating mechanism 21A is actuated to raise the stand 20A to a situation where the applying roller 17 is in contact with (is pressed against) the moving handrail 5, and the disinfection (cleaning) treatment is started.

In Step S45, whether a predetermined time elapsed or not is judged, and when it is judged that the predetermined time elapsed, the operation goes to Step S46. In Step S46, the elevating mechanism 21A is actuated to lower the stand 20A to a prescribed position where the applying roller 17 which has been in contact with the moving handrail 5 comes off (is brought out of contact with) the moving handrail 5, and this is the completion of the disinfection treatment on the moving handrail 5 using the applying roller 17. Here, the above predetermined time is set to a previously decided uniform time, a time required for the moving handrail 5 to circuit a fixed number of times, a time decided depending on the dirt state, or the like.

On the other hand, in Step S42, when it is judged that it has not come to the prescribed dirt state, the operation goes to Step S47. In Step S47, whether a virus detection signal was input from the virus detecting unit 41 or not is judged, and when it is judged that the virus detection signal was input, the operation goes to Step S48.

In Step S48, the communications unit 50 is controlled to send information concerning the virus detection (e.g. identification information about the device itself and information about the detected virus) to the management center 100, and thereafter, the operation goes to Step S49.

In Step S49, the disinfection treatment on the moving handrail 5 using the second impregnating roller 19 moistened with the second disinfection solution 30B and the applying roller 17 is started. That is, the sliding mechanism 23A is actuated to slide the second slide plate 22B in such a manner that the second impregnating roller 19 comes in contact with the applying roller 17, while to slide the first slide plate 22A in such a manner that the first impregnating roller 18 does not come in contact with the applying roller 17. Thereafter, the elevating mechanism 21A is actuated to raise the stand 20A to a situation where the applying roller 17 is in contact with (is pressed against) the moving handrail 5, and the disinfection treatment is started.

In Step S50, whether a predetermined time elapsed or not is judged, and when it is judged that the predetermined time elapsed, the operation goes to Step S51. In Step S51, the elevating mechanism 21A is actuated to lower the stand 20A to a prescribed position where the applying roller 17 which has been in contact with the moving handrail 5 comes off (is brought out of contact with) the moving handrail 5, and the disinfection treatment on the moving handrail 5 using the applying roller 17 moistened with the second disinfection solution 30B is completed.

On the other hand, in Step S47, when it is judged that no virus detection signal has been input from the virus detecting unit 41, the operation goes to Step S52. In Step S52, based on a detection signal input from the handrail sensor 71, whether the number of persons who made contact with the moving handrail 5 after the completion of the last disinfection operation reached a predetermined number or not is judged, and when it is judged that it reached the predetermined number, the operation goes to Step S53.

In Step S53, the communications unit 50 is controlled to send information concerning the number of handrail contacting persons (e.g. identification information about the device itself, elapsed time information after the last disinfection operation and the detected handrail contacting person number information) to the management center 100, and thereafter, the treatment in Steps S44, S45 and S46, that is, the disinfection treatment on the moving handrail 5 using the applying roller 17 moistened with the first disinfection solution 30A is conducted.

On the other hand, in Step S52, when it is judged that it has not reached the predetermined number, the operation goes to Step S54. In Step S54, whether a predetermined time (e.g. several hours) elapsed after the last disinfection operation or not is judged, and when it is judged that the predetermined time has not elapsed, the operation is finished, while when it is judged that the predetermined time elapsed, the treatment in Steps S44, S45 and S46, that is, the disinfection treatment on the moving handrail 5 using the applying roller 17 moistened with the first disinfection solution 30A is conducted.

Here, after the above-described disinfection treatment operation, the refilling/replacement treatment operation of the disinfection solutions to the first disinfection solution tank 32A and the second disinfection solution tank 32B is conducted.

Using the moving handrail disinfecting device 10B according to the embodiment, when a virus was detected by the virus detecting unit 41, the roller to be allowed to make contact with the applying roller 17 can be switched from the first impregnating roller 18 to the second impregnating roller 19, resulting in appropriate disinfection of the surface of the moving handrail 5 with the second disinfection solution 30B having a high disinfection effect. For example, when disinfection is highly required on public health, such as when the influenza virus, the noro-virus or the like was detected, it is possible to conduct disinfection sufficiently with good timing, leading to enhanced public health. It becomes possible to suitably use two kinds of disinfection solutions depending on the situations of the disinfecting device concerned and the like, leading to appropriate disinfection treatment with little waste depending on the situations.

Since the timing and time of the disinfection operation with the first disinfection solution 30A by allowing the first impregnating roller 18 to make contact with the applying roller 17 is controlled based on the number of handrail contacting persons detected by the handrail sensor 71, the disinfection of each of the moving handrails 5 arranged on both sides can be separately conducted at an appropriate frequency based on the accumulated number of persons which made contact with the moving handrail 5 and the like. As a result, it becomes possible to prevent the disinfection (cleaning) treatment from being conducted more than necessary, leading to a reduction in maintenance cost such as disinfection solution cost.

Since the communications unit 50 is included therein, various kinds of information obtained by the disinfecting device concerned (information concerning the dirt state detected by the dirt detecting unit 40, the detection state of the virus detected by the virus detecting unit 41, the handrail contacting person number detected by the handrail sensor 71, the time of replacement of the applying roller 17, the first impregnating roller 18 and the second impregnating roller 19, the time of replacement/refilling of the disinfection solution tanks 32A and 32B, etc.) can be sent to the management center 100.

In the management center 100, for example, it becomes possible to centrally manage information about a plurality of moving handrail disinfecting devices 10B installed on each escalator 1 in a facility, and it becomes possible to perform required maintenance with proper timing on every moving handrail disinfecting device 10B based on these items of information, leading to improved information shareability and maintenance performance.

In the moving handrail disinfecting device 10B, since the bearing portions 20d of the applying roller 17, the bearing portions 22d of the first impregnating roller 18 and the bearing portions (not shown) of the second impregnating roller 19 are constructed in such a manner that rotation sliding resistance is given to the rotation movement of the rotation shaft of each roller, it is possible to regulate the rotation rate of the applying roller 17 to be slower than the moving rate of the moving handrail 5. By causing the rotation sliding resistance (a slippage state) between the applying roller 17 and the moving handrail 5, the efficiency of applying disinfection solutions, that of removing dirt and the like can be enhanced.

Here, in the above-described moving handrail disinfecting device 10B, the dirt detecting unit 40 and the virus detecting unit 41 are arranged, but in another embodiment, it is possible to arrange a virus detecting unit 41 while to arrange no dirt detecting unit 40. By such construction, only when a prescribed virus was detected by the virus detecting unit 41, the roller to be allowed to make contact with an applying roller 17 may be switched from a first impregnating roller 18 to a second impregnating roller 19 to conduct a disinfection operation with a second disinfection solution 30B for a predetermined time. Under normal conditions besides that, the first impregnating roller 18 may be allowed to make contact with the applying roller 17 to continuously go on with the disinfection (cleaning) treatment on a moving handrail 5 using the applying roller 17 moistened with a first disinfection solution 30A.

In still another embodiment, with no dirt detecting unit 40 and no virus detecting unit 41 arranged, based on detection signals from a handrail sensor 71, the switching of a roller to be allowed to make contact with an applying roller 17 may be conducted. For example, when the number of handrail contacting persons reached a predetermined number, a first impregnating roller 18 may be allowed to make contact with the applying roller 17 to conduct disinfection (cleaning) with a first disinfection solution 30A, while when a predetermined time elapsed, a second impregnating roller 19 may be allowed to make contact with the applying roller 17 to periodically conduct disinfection with a second disinfection solution 30B.

In place of the handrail sensor 71, a human body sensor (a sensor operable to detect a person who gets on an escalator 1 which is installed in the vicinity of a landing of the escalator 1 or else) may be used. The human body sensor comprises an infrared sensor, an image sensor and associated parts, and a signal detected by the human body sensor may be output to a control unit 60B. It is also possible to separately detect persons positioning on the right side and on the left side of the steps of an escalator 1 by installing a plurality of human body sensors.

When the timing and time of the disinfection operation are controlled based on the passenger number detected by the human body sensor, it is possible to disinfect a moving handrail 5 at an appropriate frequency based on the accumulated number of passengers. As a result, the disinfection treatment can be prevented from being conducted more than necessary, leading to a reduction in maintenance cost such as disinfection solution cost.

In a management center 100, the accumulated number of passengers detected by the human body sensor of each disinfecting device can be managed, and it becomes possible to perform required maintenance with proper timing on every disinfecting device.

In another embodiment of the moving handrail disinfecting device 10B according to the above embodiment, a drying unit which promotes drying of an applied disinfection solution by blowing a hot wind onto the surface of a moving handrail 5 or the like may be arranged. Or a wiping member for wiping away an extra amount of a disinfection solution attached to the surface of the moving handrail 5 may be arranged.

The moving handrail disinfecting devices 10B may be applied to other passenger conveyors such as so-called moving pavements, which allow passengers to go in a horizontal direction or in a slightly inclined direction.

What is claimed is:

1. A moving handrail disinfecting device for passenger conveyor, comprising:
    a disinfecting unit for disinfecting a moving handrail of a passenger conveyor, being installed outside at least one of handrail inlets on each side of drawing and delivery of said moving handrail; and
    a control unit operable to control disinfection operations by the disinfecting unit based on prescribed operating conditions,
    the disinfecting unit comprising:
    an applying roller to be allowed to make contact with the moving handrail;
    a first impregnating roller to be allowed to make contact with said applying roller to supply a first disinfection solution;
    a second impregnating roller to be allowed to make contact with the applying roller to supply a second disinfection solution; and
    a contact roller switching unit operable to switch a roller to be allowed to make contact with the applying roller to the first impregnating roller or the second impregnating roller,
    said contact roller switching unit comprising:
    a first slide section on which a first disinfection solution tab with the first impregnating roller arranged is placed;
    a second slide section on which a second disinfection solution tab with the second impregnating roller arranged is placed; and
    a sliding mechanism operable to separately slide the first slide section and the second slide section,
    wherein the control unit has a function of controlling the sliding mechanism to slide the first slide section and the second slide section so as to switch the roller to be allowed to make contact with the applying roller to the first impregnating roller or the second impregnating roller, when a prescribed switching condition was satisfied.

2. The moving handrail disinfecting device for passenger conveyor according to claim 1, further comprising:
    an elevating unit operable to raise and lower the disinfecting unit in a manner that can selectively allow the applying roller to make contact with the moving handrail,
    wherein the control unit has a function of controlling the sliding mechanism to slide the first slide section and the second slide section and then controlling the elevating unit to raise the disinfecting unit until the applying roller is pressed against the moving handrail.

3. The moving handrail disinfecting device for passenger conveyor according to claim 1, wherein bearing portions of the applying roller, bearing portions of the first impregnating roller and bearing portions of the second impregnating roller are constructed in a manner that gives rotation sliding resistance to the rotation movement of each of the rollers.

4. The moving handrail disinfecting device for passenger conveyor according to claim 1, further comprising:
    a communications unit operable to send information obtained by said disinfecting device to an outside management center; and
    a dirt detecting unit operable to detect dirt on the surface of the moving handrail,
    wherein the control unit controls the timing and time of a disinfection operation by the disinfecting unit based on the state of dirt detected by the dirt detecting unit; and
    the control unit controls the communications unit to send information about the state of dirt detected by the dirt detecting unit to the management center.

5. The moving handrail disinfecting device for passenger conveyor according to claim 1, further comprising:
    a communications unit operable to send information obtained by said disinfecting device to an outside management center; and
    a passenger number detecting unit operable to detect the number of persons boarding the passenger conveyor,
    wherein the control unit controls the timing and time of a disinfection operation by the disinfecting unit based on the accumulated number of passengers detected by the passenger number detecting unit; and
    the control unit controls the communications unit to send information about the accumulated number of passengers detected by the passenger number detecting unit to the management center.

6. The moving handrail disinfecting device for passenger conveyor according to claim 1, further comprising:
    a communications unit operable to send information obtained by said disinfecting device to an outside management center; and
    a handrail contact detecting unit operable to detect a contact of a part of a body with the moving handrail,
    wherein the control unit controls the timing and time of a disinfection operation by the disinfecting unit based on the detection state of handrail contact detected by the handrail contact detecting unit; and
    the control unit controls the communications unit to send information about the detection state of handrail contact detected by the handrail contact detecting unit to the management center.

7. The moving handrail disinfecting device for passenger conveyor according to claim 1, further comprising:
    a communications unit operable to send information obtained by said disinfecting device to an outside management center; and
    a virus detecting unit operable to detect a prescribed virus sticking to the surface of the moving handrail,
    wherein the control unit controls the timing and time of a disinfection operation by the disinfecting unit based on the detection state of the virus detected by the virus detecting unit; and
    the control unit controls the communications unit to send information about the detection state of the prescribed virus detected by the virus detecting unit to the management center.

8. The moving handrail disinfecting device for passenger conveyor according to claim 2, wherein bearing portions of the applying roller, bearing portions of the first impregnating roller and bearing portions of the second impregnating roller are constructed in a manner that gives rotation sliding resistance to the rotation movement of each of the rollers.

9. The moving handrail disinfecting device for passenger conveyor according to claim 2, further comprising:
- a communications unit operable to send information obtained by said disinfecting device to an outside management center; and
- a dirt detecting unit operable to detect dirt on the surface of the moving handrail,
- wherein the control unit controls the timing and time of a disinfection operation by the disinfecting unit based on the state of dirt detected by the dirt detecting unit; and
- the control unit controls the communications unit to send information about the state of dirt detected by the dirt detecting unit to the management center.

10. The moving handrail disinfecting device for passenger conveyor according to claim 2, further comprising:
- a communications unit operable to send information obtained by said disinfecting device to an outside management center; and
- a passenger number detecting unit operable to detect the number of persons boarding the passenger conveyor,
- wherein the control unit controls the timing and time of a disinfection operation by the disinfecting unit based on the accumulated number of passengers detected by the passenger number detecting unit; and
- the control unit controls the communications unit to send information about the accumulated number of passengers detected by the passenger number detecting unit to the management center.

11. The moving handrail disinfecting device for passenger conveyor according to claim 2, further comprising:
- a communications unit operable to send information obtained by said disinfecting device to an outside management center; and
- a handrail contact detecting unit operable to detect a contact of a part of a body with the moving handrail,
- wherein the control unit controls the timing and time of a disinfection operation by the disinfecting unit based on the detection state of handrail contact detected by the handrail contact detecting unit; and
- the control unit controls the communications unit to send information about the detection state of handrail contact detected by the handrail contact detecting unit to the management center.

12. The moving handrail disinfecting device for passenger conveyor according to claim 2, further comprising:
- a communications unit operable to send information obtained by said disinfecting device to an outside management center; and
- a virus detecting unit operable to detect a prescribed virus sticking to the surface of the moving handrail,
- wherein the control unit controls the timing and time of a disinfection operation by the disinfecting unit based on the detection state of the virus detected by the virus detecting unit; and
- the control unit controls the communications unit to send information about the detection state of the prescribed virus detected by the virus detecting unit to the management center.

* * * * *